(12) United States Patent
Duvall et al.

(10) Patent No.: US 9,840,729 B2
(45) Date of Patent: Dec. 12, 2017

(54) AZO MEDIATORS AND METHODS OF USE THEREOF

(71) Applicant: Roche Diabetes Care, Inc., Indianapolis, IN (US)

(72) Inventors: Stacy H. Duvall, Indianapolis, IN (US); Peter Gebauer, Penzberg (DE); Dieter Heindl, Munich (DE); Carina Horn, Biblis (DE); Peter Kratzsch, Penzberg (DE); Michael Marquant, Mannheim (DE); Thomas Meier, Munich (DE)

(73) Assignee: Roche Diabetes Care, Inc., Indianapolis, IN (US)

(*) Notice: Subject to any disclaimer, the term of this patent is extended or adjusted under 35 U.S.C. 154(b) by 8 days.

(21) Appl. No.: 14/226,884

(22) Filed: Mar. 27, 2014

(65) Prior Publication Data
US 2014/0212903 A1    Jul. 31, 2014

Related U.S. Application Data

(63) Continuation of application No. PCT/EP2012/068951, filed on Sep. 26, 2012.

(30) Foreign Application Priority Data

Sep. 28, 2011    (EP) ..................... 11183111

(51) Int. Cl.
*C12Q 1/54*    (2006.01)
*C07D 295/215*    (2006.01)
*C07C 281/20*    (2006.01)

(52) U.S. Cl.
CPC ............. *C12Q 1/54* (2013.01); *C07C 281/20* (2013.01); *C07D 295/215* (2013.01)

(58) Field of Classification Search
CPC ........................................ C12Q 1/54
See application file for complete search history.

(56) References Cited

U.S. PATENT DOCUMENTS

| 3,491,084 A | 1/1970 | Huenig et al. |
| 5,206,147 A | 4/1993 | Hoenes |
| 5,286,362 A | 2/1994 | Hoenes et al. |
| 2012/0152763 A1 | 6/2012 | Takahara et al. |

FOREIGN PATENT DOCUMENTS

| JP | 10-203028 A | 4/1998 |
| JP | 10-265691 A | 6/1998 |

OTHER PUBLICATIONS

Eicher, Th et al., "The Synthesis of Carbonylazo Compounds by the Reaction of Alkoxydiazenium Salts with Carboxylates," Angewandte Chemie International Edition, 1967, pp. 699, vol. 6, No. 8.
Kosower, Edward M. and Miyadera, Tetsuo, "Gluthathione. 6. Probable Mechanism of Action of Diazene Antibiotics," Journal of Medicinal Chemistry, 1972, pp. 307-312, vol. 15, No. 3.

*Primary Examiner* — Joseph R Kosack

(57) ABSTRACT

Azo compounds are disclosed that do not form azoxy dimers and that do not have any reactive nitroso groups. Also disclosed are use of the azo compounds as mediators in optical and electrochemical diagnostic methods, as well as detection reagents, kits and test elements that include such azo compounds and that can be used in the diagnostic methods.

9 Claims, 4 Drawing Sheets

(Mediator 7 + 15 Eq. ascorbic acid)

(Mediator 7 + 15 Eq. carba NADH Na$_2$)

AZO MEDIATORS AND METHODS OF USE THEREOF

CROSS-REFERENCE TO RELATED APPLICATIONS

This patent application is a continuation of Int'l Patent Application No. PCT/EP2012/068951; filed 26 Sep. 2012, which claims priority to and the benefit of EP Patent Application No. 11183111.1; filed 28 Sep. 2011. Each patent application is incorporated herein by reference as if set forth in its entirety.

TECHNICAL FIELD

This disclosure relates generally to chemistry and medicine, and more particularly, it relates to azo compounds and their use as mediators in diagnostic methods. In addition, it relates to detecting reagents, kits and test elements incorporating the azo compounds.

BACKGROUND

Diagnostic test elements are important components of clinically relevant methods for determining an analyte presence or concentration. An example of such methods is a rapid and precise enzyme-based determination of analyte concentration. In this manner, the analyte to be determined is contacted with a suitable enzyme, a coenzyme and optionally a mediator, where the coenzyme is physicochemically changed (e.g., oxidized or reduced) and subsequently detected by suitable methods.

When a mediator is used, it transfers redox equivalents released during enzymatic conversion of the analyte from the physicochemically changed coenzyme to an optical indicator or conductive components of an electrode for photometric or electrochemical detection, respectively. A calibration of a measured value then yields a direct relationship with the analyte concentration to be determined.

Mediators are known for use in test elements to determine analyte concentration and include, for example, potassium hexacyanoferrate, ferrocene derivatives, quinones, oxazines, phenazines and thiazines. A review of mediators that directly transfer redox equivalents to a suitable detection system and that can be used for electrochemically determining blood glucose may be found in, for example, Takaminami (2008) *Mater. Integr.* 21:317-323 and Heller et al. (2008) *Chem. Rev.* 108:2482-2505.

Other mediators can nitrosoanilines, such as those disclosed in U.S. Pat. Nos. 5,206,147 and 5,286,362. When compared to the mediators described above that enable a direct transfer of redox equivalents, nitrosoanilines are characterized in that firstly a precursor compound of the actual mediator is prepared, which then is reduced to the effective mediator that has an advantage of avoiding blank reactions.

A problem, however, when using nitrosoanilines is that they tend to form azoxy dimers and to have a high reactivity towards substances containing amino groups and mercapto groups. See, e.g., Hinson (1986) *Adv. Exp. Med. Biol.* 197:691-696). Use of nitrosoanilines thus can lead to undesired side reactions and adversely affect the specificity and sensitivity of the analyte concentration determination.

For the foregoing reasons, there is a need for mediators that lack the disadvantages noted above.

BRIEF SUMMARY

In view of the disadvantages noted above, this disclosure describes azo compounds and methods of determining an analyte concentration that use the azo compounds as mediators. An inventive concept described herein includes modified azo compounds that do not form azoxy dimers and that do not have any reactive nitroso groups. Thus, the present disclosure provides azo-based mediators for qualitatively and/or quantitatively determining an analyte presence or concentration in which the disadvantages of the prior art are at least partially eliminated. In particular, the azo-based mediators are designed such that the occurrence of blank reactions such as, for example, a reduction of the mediator by ascorbic acid is avoided and at the same time the formation of by-products such as, for example, dimers of the mediator or of products of an uncontrolled reaction of the mediator and a substance containing an amino group and/or a mercapto group is minimized. Furthermore, the azo-based mediators are more resistant to hydrolysis when compared to nitrosoanilines while having an acceptable reaction rate. The inventive concept is embodied in exemplary azo compounds, compositions such as mediators and detection reagents, as well as kits, test elements, and methods as described herein.

In one aspect, azo compounds of the general formula (I) are provided:

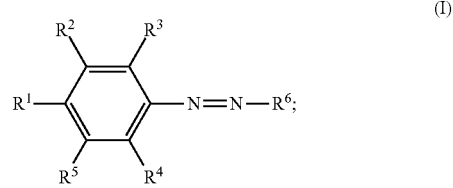

where $R^1$ denotes a residue selected from OH, $OR^7$, $SR^7$, $NHR^7$ and $NR^7R^8$;

where $R^2$, $R^3$, $R^4$ and $R^5$ independently of one another denote a residue selected from H, alkyl, cycloalkyl, alkenyl, alkinyl, aryl, heterocycloalkyl, heteroaryl, CN, COO$^-$, halogen, O(alkyl), O(aryl), NH(alkyl), N(alkyl)$_2$, N(alkyl)$_3^+$, NH(aryl), N(aryl)$_2$, NO$_2$ and SO$_3^-$, and where the alkyl, cycloalkyl, alkenyl, alkinyl, aryl, heterocycloalkyl, heteroaryl, O(alkyl), O(aryl), NH(alkyl), N(alkyl)$_2$, N(alkyl)$_3^+$, NH(aryl) or N(aryl)$_2$ can contain one or more substituents selected from COO$^-$, N(alkyl)$_3^+$, NH—C(=NH$_2$)—NH$_2^+$, OH, O—(CH$_2$CH$_2$)$_n$—OH, O—(CH$_2$CH$_2$)$_n$—O(alkyl), OPO$_3^{2-}$, PO$_3^{2-}$ and SO$_3^-$;

where $R^6$ denotes a residue selected from CN, C(=X)NH$_2$, C(=X)NHR$^9$, C(=X)NR$^9$R$^{10}$, C(=X)NHOH and C(=X)R$^9$;

where $R^7$ denotes a residue selected from alkyl, cycloalkyl, alkenyl, alkinyl, aryl, heterocycloalkyl and heteroaryl, and where the alkyl, cycloalkyl, alkenyl, alkinyl, aryl, heterocycloalkyl or heteroaryl can contain one or more substituents selected from CN, COO$^-$, halogen, NH$_2$, NH(alkyl), NH(alkyl)$_2$, N(alkyl)$_3^+$, NH(aryl), N(aryl)$_2$, NH$_2^+$, NH—C(=NH$_2$)—NH$_2^+$, NO$_2$, OH, O—(CH$_2$CH$_2$)$_n$—OH, O—(CH$_2$CH$_2$)$_n$—O(alkyl), O(alkyl), O(aralkyl), O(aryl), OPO$_3^{2-}$, PO$_3^{2-}$ and SO$_3^-$;

where $R^8$ denotes a residue selected from alkyl, cycloalkyl, alkenyl, alkinyl, aryl, heterocycloalkyl and heteroaryl, and where the alkyl, cycloalkyl, alkenyl, alkinyl, aryl, heterocycloalkyl or heteroaryl can contain one or more substituents selected from CN, COO$^-$, halogen, NH$_2$, NH(alkyl), NH(alkyl)$_2$, N(alkyl)$_3^+$, NH(aryl), N(aryl)$_2$, NH$_2^+$, NH—C(=NH$_2$)—NH$_2^+$, NO$_2$, OH, O—(CH$_2$ $CH_2)_n$—OH, O—$(CH_2CH_2)_n$—O(alkyl), O(alkyl), O(aralkyl), O(aryl), $OPO_3^{2-}$, $PO_3^{2-}$ and $SO_3^-$;

alternatively where $R^7$ and $R^8$ together with the N atom to which they are bound form a 5-membered to 7-membered heterocycle, and where the heterocycle can contain a further heteroatom selected from N, O and S and/or one or more substituents selected from CN, $COO^-$, halogen, $NH_2$, NH(alkyl), $N(alkyl)_2$, $N(alkyl)_3^+$, NH(aryl), $N(aryl)_2$, NH—C(=$NH_2$)—$NH_2^+$, $NO_2$, OH, O—$(CH_2CH_2)_n$—OH, O—$(CH_2CH_2)_n$—O(alkyl), O(alkyl), O(aralkyl), O(aryl), $OPO_3^{2-}$, $PO_3^{2-}$ and $SO_3^-$;

where $R^9$ and $R^{10}$ independently of one another denote a residue selected from alkyl, cycloalkyl, alkenyl, alkinyl, aryl, heterocycloalkyl and heteroaryl, and where the alkyl, cycloalkyl, alkenyl, alkinyl, aryl, heterocycloalkyl or heteroaryl can contain one or more substituents selected from CN, $COO^-$, halogen, $NH_2$, NH(alkyl), $N(alkyl)_2$, $N(alkyl)_3^+$, NH(aryl), $N(aryl)_2$, NH—C(=$NH_2$)—$NH_2^+$, $NO_2$, OH, O—$(CH_2CH_2)_n$—OH, O—$(CH_2CH_2)_n$—O(alkyl), O(alkyl), O(aralkyl), O(aryl), $OPO_3^{2-}$, $PO_3^{2-}$ and $SO_3^-$;

alternatively where $R^9$ and $R^{10}$ together with the N atom to which they are bound form a 5-membered to 7-membered heterocycle, and where the heterocycle can contain a further heteroatom selected from N, O and S and/or one or more substituents selected from CN, $COO^-$, halogen, $NH_2$, NH(alkyl), $N(alkyl)_2$, $N(alkyl)_3^+$, NH(aryl), $N(aryl)_2$, NH—C(=$NH_2$)—$NH_2^+$, $NO_2$, OH, O—$(CH_2CH_2)_n$—OH, O—$(CH_2CH_2)_n$—O(alkyl), O(alkyl), O(aralkyl), O(aryl), $OPO_3^{2-}$, $PO_3^{2-}$ and $SO_3^-$; and where X denotes a heteroatom selected from O and S; and where n denotes an integer from 1 to 6; provided that at least two residues selected from $R^2$, $R^3$, $R^4$ and $R^5$ denote a H atom.

In some instances, the azo compound can be the general formula (I), where $R^1$ denotes the $NR^7R^8$ residue.

In some instances, at least three residues selected from $R^2$, $R^3$, $R^4$ and $R^5$ denote a H atom, while the fourth residue can denote any residue selected from H, alkyl, cycloalkyl, alkenyl, alkinyl, aryl, heterocycloalkyl, heteroaryl, CN, $COO^-$, halogen, O(alkyl), O(aryl), NH(alkyl), $N(alkyl)_2$, $N(alkyl)_3^+$, NH(aryl), $N(aryl)_2$, $NO_2$ and $SO_3$, where the alkyl, cycloalkyl, alkenyl, alkinyl, aryl, heterocycloalkyl, heteroaryl, O(alkyl), O(aryl), NH(alkyl), $N(alkyl)_2$, $N(alkyl)_3^+$, NH(aryl) or $N(aryl)_2$ can be substituted as defined above.

In some instances, when $R^3$, $R^4$ and $R^5$ denote a H atom, then $R^2$ denotes a residue selected from H and O(alkyl). In other instances, $R^2$, $R^3$, $R^4$ and $R^5$ all denote a H atom.

In some instances, $R^6$ denotes a residue selected from C(=X)$NR^9R^{10}$ and C(=X)NHOH. In other instances, $R^6$ is C(=X)$NR^9R^{10}$, such as C(=O)$NR^9R^{10}$.

In some instances, $R^7$ denotes an alkyl residue containing one or more hydrophilic substituents selected from $COO^-$, $N(alkyl)_3^+$, NH—C(=$NH_2$)—$NH_2^+$, OH, O—$(CH_2CH_2)_n$—OH, O—$(CH_2CH_2)_n$—O(alkyl), $OPO_3^{2-}$, $PO_3^{2-}$ and $SO_3^-$ to improve water solubility of the azo compounds. In other instances, the alkyl contains one or more OH groups as hydrophilic substituent(s).

In some instances, $R^8$ denotes a residue selected from alkyl, cycloalkyl, alkenyl, alkinyl, aryl, heterocycloalkyl and heteroaryl, where the alkyl, cycloalkyl, alkenyl, alkinyl, aryl, heterocycloalkyl or heteroaryl contains one or more hydrophilic substituents selected from $COO^-$, $N(alkyl)_3^+$, NH—C(=$NH_2$)—$NH_2^+$, OH, O—$(CH_2CH_2)_n$—OH, O—$(CH_2CH_2)_n$—O(alkyl), $OPO_3^{2-}$, $PO_3^{2-}$ and $SO_3^-$. In other instances, $R^8$ denotes an alkyl residue containing one or more hydrophilic substituents selected from $COO^-$, $N(alkyl)_3^+$, NH—C(=$NH_2$)—$NH_2^+$, OH, O—$(CH_2CH_2)_n$—OH, O—$(CH_2CH_2)_n$—O(alkyl), $OPO_3^{2-}$, $PO_3^{2-}$ and $SO_3^-$. In other instances, the alkyl contains one or more OH groups as hydrophilic substituent(s).

In some instances, $R^7$ and/or $R^8$ denote a hydroxyethyl residue.

In some instances, $R^9$ and $R^{10}$ independently of one another denote a residue selected from an alkyl and aryl, where the alkyl or aryl can contain one or more substituents selected from OH, O(alkyl) and O(aryl). In other instances, $R^9$ and $R^{10}$ independently of one another denote a residue selected from methyl, ethyl, phenyl, hydroxymethyl, hydroxyethyl, hydroxyphenyl and methoxyphenyl, particularly methyl, ethyl and hydroxyethyl.

Alternatively, $R^9$ and $R^{10}$ together with the N atom to which they are bound form a 5-membered or 6-membered heterocycle, where the heterocycle can contain a further heteroatom selected from N, O and S and/or one or more substituents selected from CN, $COO^-$, halogen, $NH_2$, NH(alkyl), $N(alkyl)_2$, $N(alkyl)_3^+$, NH(aryl), $N(aryl)_2$, NH—C(=$NH_2$)—$NH_2^+$, $NO_2$, OH, O(alkyl), O—$(CH_2CH_2)_n$—OH, O—$(CH_2CH_2)_n$—O(alkyl), O(aralkyl), O(aryl), $OPO_3^{2-}$, $PO_3^{2-}$ and $SO_3^-$. When substituted, the 5- or 6-membered heterocycle can contain one or more hydrophilic substituents selected from $COO^-$, $N(alkyl)_3^+$, NH—C(=$NH_2$)—$NH_2^+$, OH, O—$(CH_2CH_2)_n$—OH, O—$(CH_2CH_2)_n$—O(alkyl), $OPO_3^{2-}$, $PO_3^{2-}$ and $SO_3^-$.

In some instances, X denotes an O atom.

The azo compounds as described herein, excluding 2-(ethyl-{3-methyl-4-[(piperidin-1-ylcarbonyl)diazenyl]phenyl}-amino)ethanol, naturally do not form azoxy dimers, which is in contrast to known nitrosoaniline mediators. Moreover, the azo compounds as described herein do not have any reactive nitroso groups by means of which a reaction could take place with substances containing amino groups and/or mercapto groups such as for example with enzymes.

The azo compounds as described herein, however, are precursor compounds from which the actual mediator is formed by subsequent reduction. Thus, the azo compounds have the known advantage for nitrosoanilines of avoiding blank reactions while at the same time also avoiding undesired side reactions such as those observed when determining analytes.

In another aspect, azo-based mediators are provided for qualitatively and/or quantitatively determining an analyte presence or concentration in a sample such as, for example, in an optical or electrochemical diagnostic method, where the azo-based mediators include the azo compounds as described herein. The azo compounds can be present as monomers or polymers and can be used in a free from as well as in a bound form. In some instances, the azo compounds can be in the form of a detection reagent that includes the azo compounds acting as a mediator coupled to other components of a suitable detection reagent such as, for example, enzymes, coenzymes and optical indicators. In other instances, the azo compounds can be immobilized on a carrier such as, for example, an electrode of a test element.

In another aspect, detection reagents are provided for determining an analyte presence or concentration, where the detection reagents can include:

(a). a flavin-, nicotinamide- or pyrroloquinolinequinone-dependent oxidoreductase, (b). a reducible flavin, nicotinamide or pyrroloquinolinequinone coenzyme, (c). an azo compound as described herein, and (d). optionally a reducible optical indicator.

The enzyme used in the detection reagents can be selected from any flavin-, nicotinamide- or pyrroloquinoline quinone-dependent oxidoreductase. In some instances, the flavin-, nicotinamide- or pyrroloquinoline quinone-dependent oxidoreductase can be a flavin-, nicotinamide- or pyrroloquinoline quinone-dependent dehydrogenase such as, for example, an alcohol dehydrogenase, glucose dehydrogenase, glucose-6-phosphate dehydrogenase, glycerol dehydrogenase, lactate dehydrogenase or malate dehydrogenase. In other instances, the detection reagent is a nicotinamide-dependent glucose dehydrogenase or glucose-6-phosphate dehydrogenase.

The reducible flavin, nicotinamide or pyrroloquinoline quinone coenzyme can be selected from flavin adenine dinucleotide (FAD), flavin mononucleotide (FMN), nicotinamide adenine dinucleotide ($NAD^+$), nicotinamide adenine dinucleotide phosphate ($NADP^+$), pyrroloquinoline quinone (PQQ) and derivatives thereof. In some instances, the coenzyme is $NAD^+$, $NADP^+$ or derivatives thereof.

When derivatives of $NAD^+$ or $NADP^+$ are used, they can be stabilized compounds (i.e., chemical derivatives of native $NAD^+$ and $NADP^+$). In some instances, the stabilized $NAD^+$ or $NADP^+$ compounds include carbacyclic analogues such as carba$NAD^+$ and carba$NADP^+$ (as described in Slama (1988) *Biochem.* 27:183-193; Blackburn et al. (1996) *Chem. Comm.* 24:2765-2766) and U.S. Pat. No. 5,801,006, as well as Int'l Patent Application Publication Nos. WO 98/33936, WO 01/49247 and WO 2007/012494). In other instances, the reducible flavin, nicotinamide or pyrroloquinoline quinone coenzyme is $NAD^+$, $NADP^+$, carba$NAD^+$ or carba$NADP^+$.

When included, the optional reducible optical indicator can be any substance that is reducible and undergoes a visually and/or mechanically detectable change in its optical properties such as, for example, color, fluorescence, reflectance, transmission, polarization and/or refractive index. In some instances, the optical indicators can be a reducible heteropoly acid, in particular 2,18-phosphomolybdic acid.

The detection reagent can be used for qualitatively and/or quantitatively determining an analyte presence or concentration of any biological or chemical substance that can be detected optically or electrochemically. In some instances, the analyte can be selected from malic acid, alcohol, ascorbic acid, cholesterol, glucose, glycerol, urea, 3-hydroxybutyrate, lactic acid, pyruvate and triglycerides. In other instances, the analyte is glucose.

In another aspect, a kit is provided for determining an analyte presence or concentration, where the kit includes the detection reagent as described herein and a test element. The test element can be an optical or electrochemical sensor and can include an application area for applying a sample, a reaction area for reacting the analyte with the detection reagent, a detection area for determining the presence and/or concentration of the analyte in the sample, and optionally a waste area.

In another aspect, test elements are provided for determining an analyte presence or concentration, where the test elements include the detection reagent as described herein. The test elements can be optical or electrochemical sensors that can include an application area for applying the sample, a reaction area containing the detection reagent for reacting the analyte with the detection reagent, a detection area for determining the presence and/or concentration of the analyte in the sample, and optionally a waste area. In some instances, the test element can be in the form of test tapes, test discs, test pads and test strips. In other instances, the test element is in the form of a test strip. Exemplary test elements are disclosed in, for example, US Patent Application Publication Nos. 2003/0031592 and 2006/0003397; as well as U.S. Pat. Nos. 5,271,895, 6,207,000, 6,540,890, 6,755,949, 7,008,799, 7,025,836 and 7,067,320.

In view of the foregoing, and in another aspect, methods are provided for determining an analyte presence or concentration, where the method includes the steps of:

(a) contacting a sample suspected of containing or containing the analyte with a detection reagent as described herein, a kit as described herein or a test element as described herein, and (b) determining qualitatively and/or quantitatively an analyte presence and/or an analyte concentration.

The sample containing the analyte can be derived from any source. In some instances, the sample can be a body fluid such as, for example, whole blood, plasma, serum, lymph fluid, bile fluid, cerebrospinal fluid, extracellular tissue fluid, urine, as well as glandular secretions such as saliva or sweat. In other instances, the sample is whole blood, plasma or serum.

With regard to the contacting step, the sample containing the analyte can be contacted with the detection reagent, kit or test element, where the analyte is oxidized by a flavin-, nicotinamide- or pyrroloquinoline quinone-dependent oxidoreductase, the reducible flavin, nicotinamide or pyrroloquinoline quinone coenzyme is reduced and electrons of the reduced flavin, nicotinamide or pyrroloquinoline quinone coenzyme are transferred by the azo-based mediator to an optionally present optical indicator or to conductive components of an electrode.

With regard to the determining step, it is possible to use any known method of detecting enzymatic reactions that generate a measurable signal that can be evaluated and/or reading out manually by one of skill in the art and/or by means of a suitable detection device. In some instances, the analyte is determined optically or electrochemically, where such optical techniques include photometry and flourimetry.

These and other advantages, effects, features and objects of the inventive concept will become better understood from the description that follows. In the description, reference is made to the accompanying drawings, which form a part hereof and in which there is shown by way of illustration, not limitation, embodiments of the inventive concept.

BRIEF DESCRIPTION OF THE DRAWINGS

The advantages, effects, features and objects other than those set forth above will become more readily apparent when consideration is given to the detailed description below. Such detailed description makes reference to the following drawings, wherein:

FIG. 3 shows kinetics of reducing 4-[bis-(2-hydroxyethyl)-amino]-benzenediazocarbamide (7) with various reducing agents. Specifically.

Figure 1:
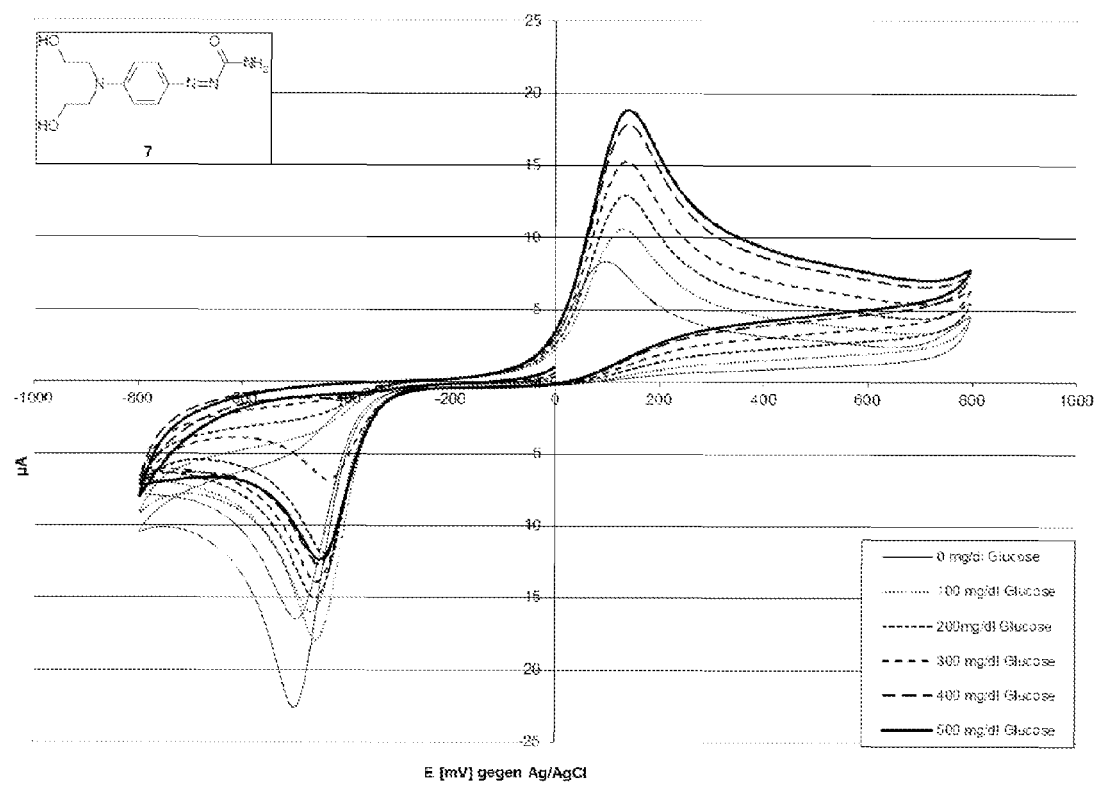
FIG. 1 is a cyclovoltagram of the azo-based mediator 4-[bis-(2-hydroxyethyl)-amino]-benzenediazocarbamide (7) in the presence of FAD-dependent glucose dehydrogenase at glucose concentrations of 0 mg/dl, 100 mg/dl, 200 mg/dl, 300 mg/dl, 400 mg/dl and 500 mg/dl. Voltage change per unit of time: 100 mV/sec.

While the inventive concept is susceptible to various modifications and alternative forms, exemplary embodiments thereof are shown by way of example in the drawings and are herein described in detail. It should be understood, however, that the description of exemplary embodiments that follows is not intended to limit the inventive concept to the particular forms disclosed, but on the contrary, the intention is to cover all advantages, effects, features and objects falling within the spirit and scope thereof as defined by the embodiments described herein and the claims below. Reference should therefore be made to the embodiments described herein and claims below for interpreting the scope of the inventive concept. As such, it should be noted that the embodiments described herein may have advantages, effects, features and objects useful in solving other problems.

DESCRIPTION OF EXEMPLARY EMBODIMENTS

The compounds, compositions, kits, test elements and methods now will be described more fully hereinafter with reference to the accompanying drawings, in which some, but not all embodiments of the inventive concept are shown. Indeed, the compounds, compositions, kits, test elements and methods may be embodied in many different forms and should not be construed as limited to the embodiments set forth herein; rather, these embodiments are provided so that this disclosure will satisfy applicable legal requirements.

Likewise, many modifications and other embodiments of the compounds, compositions, kits, test elements and methods described herein will come to mind to one of skill in the art to which the disclosure pertains having the benefit of the teachings presented in the foregoing descriptions and the associated drawings. Therefore, it is to be understood that the compounds, compositions, kits, test elements and methods are not to be limited to the specific embodiments disclosed and that modifications and other embodiments are intended to be included within the scope of the appended claims. Although specific terms are employed herein, they are used in a generic and descriptive sense only and not for purposes of limitation.

Unless defined otherwise, all technical and scientific terms used herein have the same meaning as commonly understood by one of skill in the art to which the disclosure pertains. Although any methods and materials similar to or equivalent to those described herein can be used in the practice or testing of the compounds, compositions, kits, test elements and methods, the preferred methods and materials are described herein.

Moreover, reference to an element by the indefinite article "a" or "an" does not exclude the possibility that more than one element is present, unless the context clearly requires that there be one and only one element. The indefinite article "a" or "an" thus usually means "at least one." Likewise, the terms "have," "comprise" or "include" or any arbitrary grammatical variations thereof are used in a non-exclusive way. Thus, these terms may refer both to a situation in which, besides the feature introduced by these terms, no further features are present in the entity described in this context and to a situation in which one or more further features are present. For example, the expressions "A has B," "A comprises B" and "A includes B" may refer both to a situation in which, besides B, no other element is present in A (i.e., a situation in which A solely and exclusively consists of B) and to a situation in which, besides B, one or more further elements are present in A, such as element C, elements C and D, or even further elements.

DEFINITIONS

In describing and claiming the present inventive concept, the following definitions will be used.

As used herein, "about" means within a statistically meaningful range of a value or values such as, for example, a stated concentration, molecular weight, pH, sequence identity, time frame, temperature or volume. Such a value or range can be within an order of magnitude, typically within 20%, more typically within 10%, and even more typically within 5% of a given value or range. The allowable variation encompassed by "about" will depend upon the particular system under study, and can be readily appreciated by one of skill in the art.

As used herein, "alkyl" means a saturated, linear or branched hydrocarbon residue containing about 1-12 carbon atoms that has a binding valency on any one of the 1-12 carbon atoms. In some instances, the alkyl is a hydrocarbon residue containing about 1-8 carbon atoms or about 1-6 carbon atoms. Examples of alkyls include, but are not limited to, methyl, ethyl, n-propyl, iso-propyl, n-butyl, iso-butyl, sec-butyl and tert-butyl.

As used herein, "cycloalkyl" means a saturated or unsaturated, cyclic hydrocarbon residue containing about 3-12 carbon atoms that has a binding valency on any one of the 3-12 carbon atoms. In some instances, the cycloalkyl is a cyclic hydrocarbon residue containing about 3-10 carbon atoms or about 3-8 carbon atoms. Examples of cycloalkyls include, but are not limited to, cyclopropyl, cyclobutyl, cyclopentyl, cyclohexyl, cycloheptyl and cyclooctyl.

As used herein, "alkenyl" means an unsaturated, linear or branched hydrocarbon residue containing about 2-12 carbon atoms that has a binding valency on any one of the 2-12 carbon atoms and at least one double bond. In some instances, the alkenyl is a hydrocarbon residue containing about 2-8 carbon atoms or about 2-6 carbon atoms. Examples of alkenyls include, but are not limited to, ethenyl, propenyl and butenyl.

As used herein, "alkinyl" means an unsaturated, linear or branched hydrocarbon residue containing about 2-12 carbon atoms that has a binding valency on any one of the 2-12 carbon atoms and at least one triple bond. In some instances, the alkinyl is a hydrocarbon residue containing about 2-8 carbon atoms or about 2-6 carbon atoms. Examples of alkinyls include, but are not limited to, ethinyl, propinyl and butinyl.

As used herein, "aryl" means an aromatic ring system containing about 3-14 ring atoms that solely contains carbon atoms as ring atoms and has a binding valency on any carbon atom of the 3-14 ring-forming atoms. In some instances, the aryl contains about 6-10 ring atoms. Examples of aryls include, but are not limited to, phenyl, naphthyl, anthracenyl and phenanthrenyl.

As used herein, "aralkyl" means an alkyl residue as defined above in which at least one hydrogen atom is substituted by an aryl residue as defined above. Examples of aralkyls include, but are not limited to, benzyl and phenethyl.

As used herein, "heterocycloalkyl" means a saturated or partially unsaturated ring system containing about 3-14 ring atoms, which in addition to carbon atoms contains at least one heteroatom selected from N, O and S as ring atoms and which has a binding valency on any C atom or N atom of the 3-14 ring-forming atoms. In some instances, the heterocycloalkyl contains about 5-7 ring atoms Examples of heterocycloalkyls include, but are not limited to, azepinyl, dihydrofuryl, dihydropyranyl, imidazolidinyl, imidazolinyl, isothiazolidinyl, isoxazolidinyl, morpholinyl, oxazolidinyl, piperazinyl, piperidinyl, pyrazolidinyl, pyrrolidinyl, tetrahydrofuryl, tetrahydropyranyl, thiadiazolydinyl, thiazolidinyl and thiomorpholinyl.

As used herein, "heteroaryl" means an aromatic ring system containing about 3-14 ring atoms, which in addition to carbon atoms contains at least one heteroatom selected from N, O and S as ring atoms and which has a binding valency on any C atom or N atom of the 3-14 ring-forming atoms. In some instances, the heteroaryl contains about 5-6 ring atoms. Examples of heteroaryls include, but are not limited to, furanyl, imidazolyl, isothiazolyl, isoxazolyl, oxadiazolyl, oxazolyl, pyrazolyl, pyrrolyl, tetrazolyl, thiadiazolyl, thiazolyl, thienyl, triazolyl, pyrazinyl, pyridazinyl, pyridyl, pyrimidinyl and triazinyl.

As used herein, "halogen" means bromine, chlorine, flourine and iodine.

EXAMPLES

The inventive concept will be more fully understood upon considering the following non-limiting examples, which are offered for purposes of illustration, not limitation.

If not stated otherwise the chemicals that are used are commercially available and of the highest possible commercial quality.

Example 1: Synthesis of Azo Compounds

Synthesis of 2-[(2-hydroxyethyl)-(4-nitrophenyl)-amino]-ethanol (3)

Synthesis scheme:

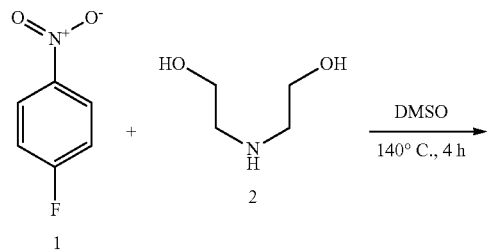

1-fluoronitrobenzene (1) (1.00 ml, 9.38 mmol) and diethanolamine (2) (2.73 ml, 28.5 mmol) were dissolved in 20.0 ml dimethyl sulfoxide (DMSO) and refluxed for 4 hours at 140° C. Afterwards, the solvent was removed under reduced pressure (3 mbar, 80° C.), and an orange-colored oil remained that was dissolved in a mixture of ethyl acetate ($C_4H_8O_2$) and water ($H_2O$). The organic phase was separated, washed several times with $H_2O$ and dried over magnesium sulfate ($MgSO_4$). After removing the solvent under reduced pressure, 1.35 g (63%) of the title compound was obtained.

Synthesis of
N,N-bis(2-hydroxyethyl)-4-aminoaniline dihydrochloride (4)

Synthesis scheme:

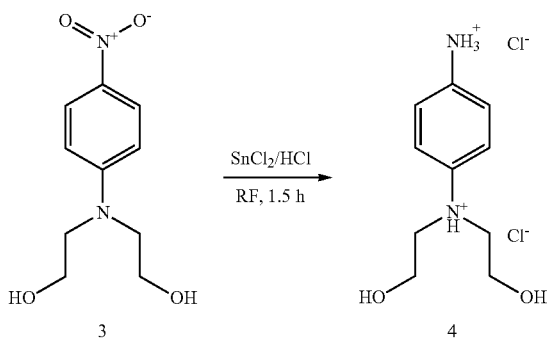

2-[(2-hydroxyethyl)-(4-nitrophenyl)-amino]-ethanol (3) (1.35 g, 5.97 mmol) was dissolved in 100 ml conc. hydrochloric acid (HCl; 37%), tin (II) chloride dihydrate ($SnCl_2.2H_2O$; 8.07 g, 26.5 mmol) was added, and it was refluxed for 1.5 h at 105° C. Afterwards, the mixture was adjusted to pH 8.5 by adding ammonia solution (25% in $H_2O$) while cooling on ice during which a colorless solid precipitated. After extracting the aqueous suspension several times with $C_4H_8O_2$, the combined organic phases were dried over sodium sulfate ($Na_2SO_4$), evaporated to a quarter of the original volume, and 3.00 ml conc. HCl (37%) was added. After removing the solvent under reduced pressure and drying the residue in a high vacuum, 590.0 mg (37%) of the title compound was obtained.

Synthesis of
4-[bis-(2-hydroxyethyl)-amino]-benzenediazocyanide (6)

Synthesis scheme:

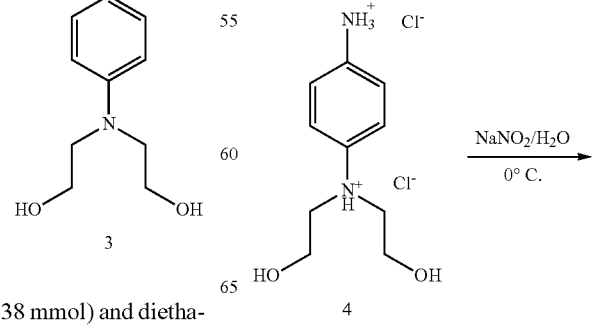

-continued

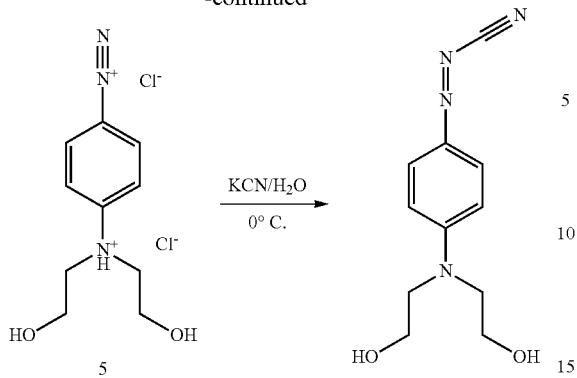

N,N-bis(2-hydroxyethyl)-4-aminoaniline dihydrochloride (4) (50.0 mg, 0.186 mmol) was dissolved in 1.80 ml H₂O and cooled to 0° C. Afterwards, a solution of sodium nitrite (NaNO₂; 38.5 mg, 0.558 mmol) in H₂O (1.90 ml) was added dropwise to this solution over a period of 30 min, whereupon the mixture changed color via red to green-brown. Subsequently, a solution of potassium cyanide (KCN; 36.3 mg, 0.558 mmol) in H₂O (0.60 ml) was added dropwise to the reaction mixture over a period of 30 min while cooling during which the color changed to red-brown. After 45 min of stirring at this temperature, the reaction mixture was extracted several times with C₄H₈O₂. The combined organic phases were dried over Na₂SO₄, and the solvent was removed under reduced pressure. A chromatographic purification of the residue on silica gel (eluant: CHCl₃/MeOH=92:8) yielded 31.4 mg (72%) of the title compound as dark red crystals.

Synthesis of 4-[bis-(2-hydroxyethyl)-amino]-benzenediazocarbamide (7)

Synthesis scheme:

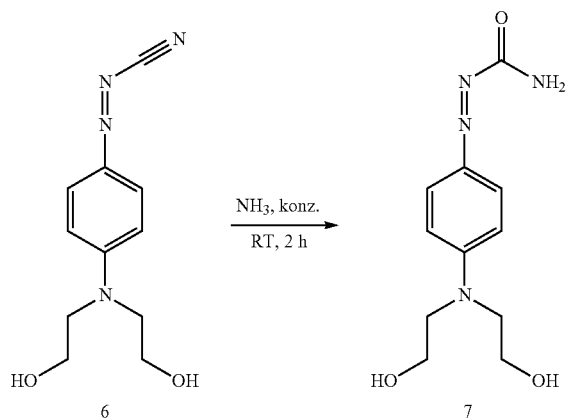

4-[bis-(2-hydroxyethyl)-amino]-benzenediazocyanide (6) (43.9 mg, 0.201 mmol) was dissolved in 15.0 ml ammonia solution (30-33% in H₂O) and stirred for 3 h at room temperature. After removing the solvent under reduced pressure, the residue was purified by means of preparative HPLC (Hypersil ODS; 0.1 M triethylammonium acetate buffer/acetonitrile gradient) to obtain 24.4 mg (38%) of the title compound in the form of the corresponding acetate salt as dark red, hygroscopic crystals.

Synthesis of 4-[bis-(2-hydroxyethyl)-amino]-benzenediazodimethylcarbamide (8)

Synthesis scheme:

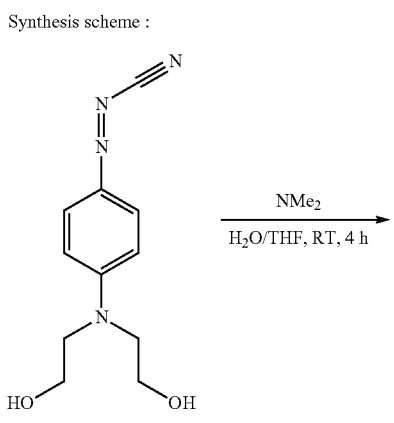

4-[bis-(2-hydroxyethyl)-amino]-benzenediazocyanide (6) (10.2 mg, 0.044 mmol) was dissolved in 2.00 ml H₂O. Afterwards, dimethylamine (2M in THF, 2.00 ml, 52.2 mmol) was added, and the reaction mixture was stirred for 4 h at room temperature. After removing the solvent under reduced pressure, the residue was purified by means of preparative HPLC (Hypersil ODS; 0.1 M triethylammonium acetate buffer/acetonitrile gradient) to obtain 7.1 mg (47%) of the title compound in the form of the corresponding monoacetate salt as dark red, hygroscopic crystals.

Synthesis of 4-[bis-(2-hydroxyethyl)-amino]-benzenediazo-bis-(2-hydroxyethyl)-carbamide (9)

Synthesis scheme:

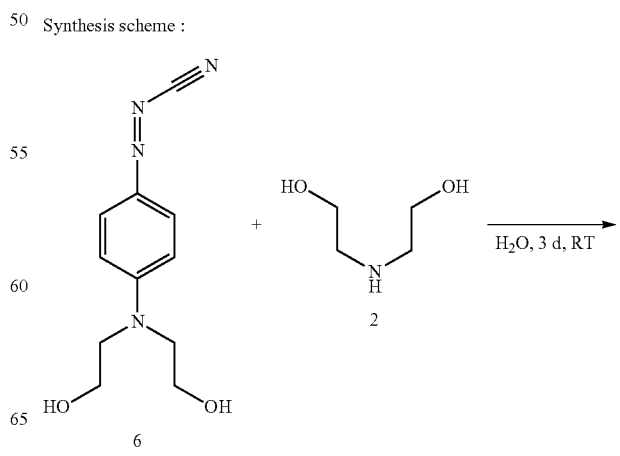

-continued

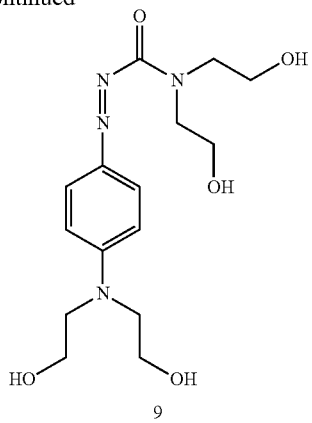

9

4-[bis-(2-hydroxyethyl)-amino]-benzenediazocyanide (6) (6.50 g, 27.75 mmol) was suspended in 520 ml $H_2O$. Afterwards, diethanolamine (2) (13.26 ml, 138.7 mmol) was added to the suspension, and the reaction mixture was stirred for 72 h at room temperature. After removing the solvent under reduced pressure, the residue was purified twice by column chromatography on silica gel (eluant: $CH_2Cl_2$/MeOH=85:15+2% $NEt_3$), followed by a further purification by column chromatography on Sephadex® LH-20 (eluant: $H_2O$). After freeze drying, 4.10 g (43%) of the title compound was obtained as a red, amorphous solid.

Synthesis of 4-(2-(4-(bis-(2-hydroxyethyl)-amino)-phenyl)-diazocarbonyl)-morpholine (11)

Synthesis scheme:

4-[bis-(2-hydroxyethyl)-amino]-benzenediazocyanide (6) (100.0 mg, 0.427 mmol) was suspended in 4.00 ml $H_2O$/MeOH (1:1). Afterwards, morpholine (744 µl, 8.54 mmol) was added to the suspension, and the reaction mixture was stirred for 16 h at room temperature. After removing the solvent under reduced pressure, the residue was purified twice by column chromatography on silica gel (eluant: $CH_2Cl_2$/MeOH=70:30+2% $Net_3$) to obtain 12.5 mg (9%) of the title compound as dark red crystals.

Synthesis of 2-(4-(Bis-(2-hydroxyethyl)-amino)-phenyl)-N-hydroxy-diazene-carboxamide (13)

Synthesis scheme:

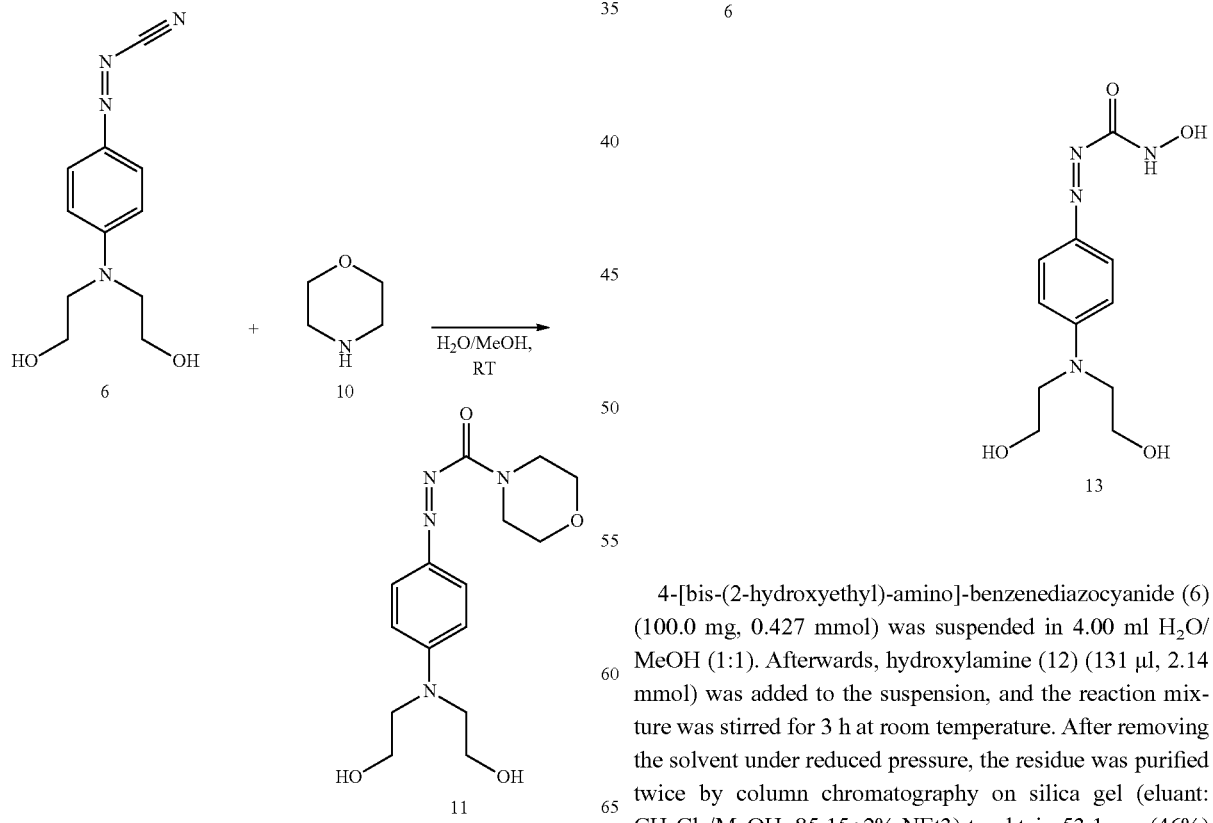

4-[bis-(2-hydroxyethyl)-amino]-benzenediazocyanide (6) (100.0 mg, 0.427 mmol) was suspended in 4.00 ml $H_2O$/MeOH (1:1). Afterwards, hydroxylamine (12) (131 µl, 2.14 mmol) was added to the suspension, and the reaction mixture was stirred for 3 h at room temperature. After removing the solvent under reduced pressure, the residue was purified twice by column chromatography on silica gel (eluant: $CH_2Cl_2$/MeOH=85:15+2% NEt3) to obtain 53.1 mg (46%) of the title compound as an orange solid.

Synthesis of 4-methoxy-benzenediazocyanide (16)

Synthesis scheme:

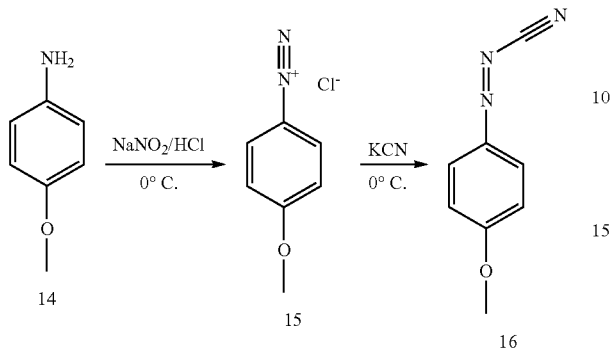

p-anisidine (14) (2.50 g, 20.30 mmol) was dissolved in aqueous HCl (1M, 40.0 ml) and cooled to 0° C. Afterwards, a solution of NaNO$_2$ (4.20 g, 60.90 mmol) in 120 ml H$_2$O was added dropwise to this solution over a period of 30 min, whereupon the reaction mixture changed to a red-brown color. Subsequently, a solution of KCN (3.97 g, 60.90 mmol) in 60.0 ml H$_2$O was added over a period of 30 min to the reaction mixture while cooling continuously during which an orange-yellow solid precipitated, which was filtered, washed once with 1 M HCl and twice with H$_2$O. The solid was dissolved in C$_4$H$_8$O$_2$, and the organic phase was washed once each time with H$_2$O and with saturated NaCl solution. After drying the organic phase over Na$_2$SO$_4$ and removing the solvent under reduced pressure, the residue was purified by column chromatography on silica gel (eluant: n-hexane/CH$_2$Cl$_2$/EtOAc=80:10:10) to obtain 850.0 mg (26%) of the title compound as orange-brown crystals.

Synthesis of 4-methoxy-benzenediazo-bis(2-hydroxyethyl)-carbamide (17)

Synthesis scheme:

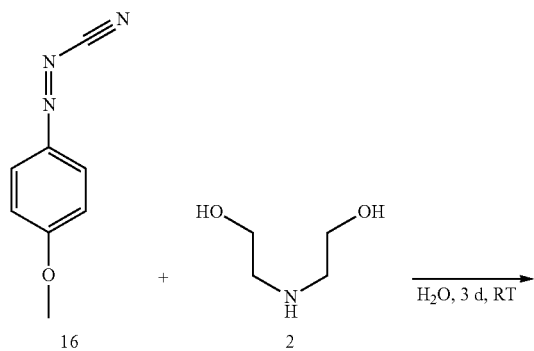

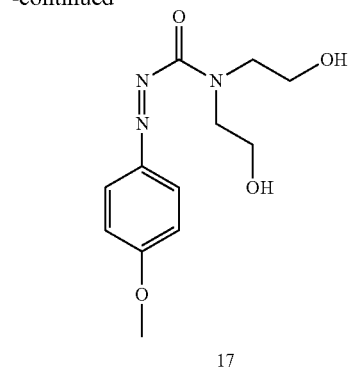

4-methoxy-benzenediazocyanide (16) (100.0 mg, 0.621 mmol) was suspended in a mixture of 2.00 ml H$_2$O and 4.00 ml MeOH. Afterwards, diethanolamine (2) (297 µl, 3.103 mmol) was added to the suspension and the reaction mixture was stirred for 72 h at room temperature. After removing the solvent under reduced pressure, the residue was purified by column chromatography on silica gel (eluant: CH$_2$Cl$_2$/MeOH=92:8) to obtain 82.3 mg (49%) of the title compound as an orange solid.

Synthesis of 2-[(2-hydroxyethyl)-(2-methoxy-4-nitrophenyl)-amino]-ethanol (19)

Synthesis scheme:

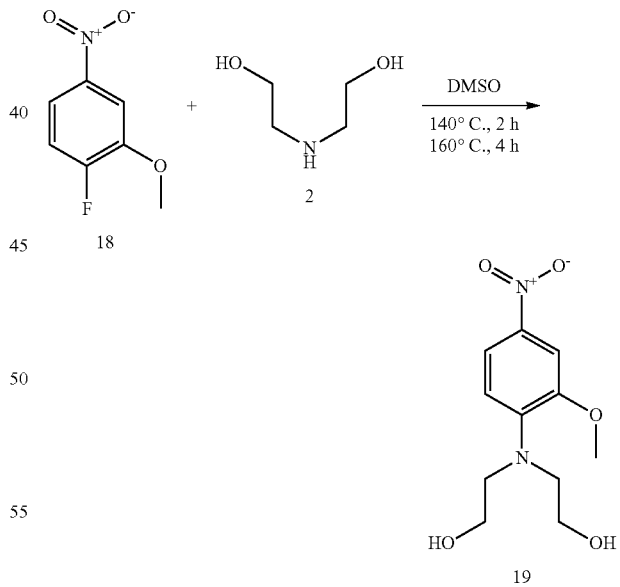

2-fluoro-5-nitroanisole (18) (2.00 g, 8.62 mmol) and diethanolamine (2) (2.48 ml, 28.48 mmol) were dissolved in 20.0 ml DMSO and refluxed for 2 h at 140° C. and for 4 h at 160° C. Afterwards, the solvent was removed under reduced pressure (3 mbar, 80° C.), whereupon a red-brown oil remained that was dissolved in a mixture of CH$_2$Cl$_2$ and H$_2$O. The aqueous phase was acidified with 2 M HCl to pH 1 and extracted several times with $CH_2Cl_2$. After filtration, the aqueous phase was adjusted with 2 M NaOH to pH 12 and again extracted with $CH_2Cl_2$. The combined organic phases were dried over $Na_2SO_4$, and the solvent was removed under reduced pressure to obtain an orange-colored oil. A chromatographic purification of the residue on silica gel (eluant: EtOAc/MeOH=95:5) yielded 136.5 mg (6%) of the title compound.

Synthesis of 2-[(4-amino-2-methoxyphenyl)-2-(2-hydroxyethyl)-amino]-ethanol dihydrochloride (20)

Synthesis scheme:

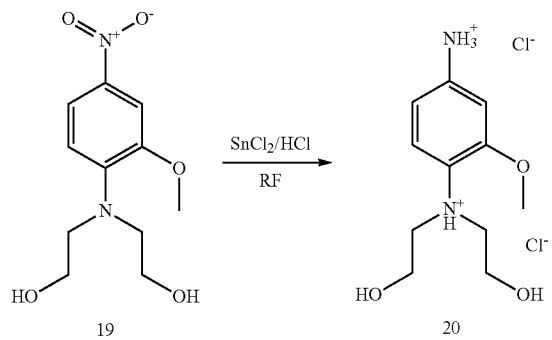

2-[(2-hydroxyethyl)-(2-methoxy-4-nitrophenyl)-amino]-ethanol (19) (136.9 mg, 0.534 mmol) was dissolved in 10.0 ml conc. HCl (37%), $SnCl_2 \cdot 2H_2O$ (723.2 mg, 3.205 mmol) was added, and it was refluxed for 2 h at 110° C. Afterwards, the mixture was adjusted to pH 8.6 by adding ammonia solution (25% in $H_2O$) while cooling on ice, whereupon a colorless solid precipitated. After extracting the aqueous suspension several times with ethyl acetate, the combined organic phases were dried over $Na_2SO_4$, evaporated to a quarter of the original volume, and 1.00 ml conc. HCl (37%) was added. After removing the solvent under reduced pressure and drying the residue in a high vacuum, 114.6 mg (71%) of the title compound (20) was obtained.

Synthesis of 4-[bis-(2-hydroxyethyl)-amino]-2-methoxy-benzenediazocyanide (22)

Synthesis scheme:

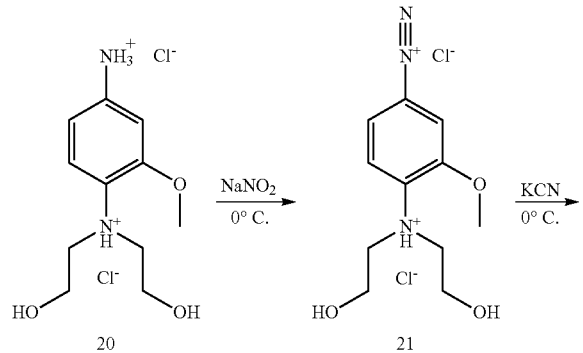

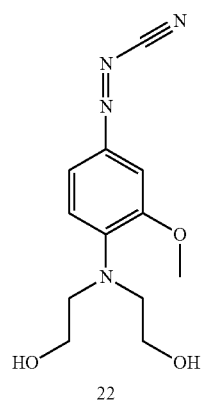

2-[(4-amino-2-methoxyphenyl)-2-(2-hydroxyethyl)-amino]-ethanol dihydrochloride (20) (55.6 mg, 0.186 mmol) was dissolved in 1.80 ml $H_2O$ and cooled to 0° C. A solution of $NaNO_2$ (38.5 mg, 0.558 mmol) in 1.90 ml $H_2O$ was added dropwise to this solution over a period of 30 min, whereupon the reaction mixture changed to a brown color. Subsequently, a solution of KCN (36.3 mg, 0.558 mmol) in 0.60 ml $H_2O$ was added to this over a period of 30 min while cooling, whereupon the color changed to deep red. After 45 min stirring at this temperature, the reaction mixture was extracted several times with ethyl acetate. The combined organic phases were dried over $Na_2SO_4$, and the solvent was removed under reduced pressure. Chromatographic purification of the residue on silica gel (eluant: $CH_2Cl_2$/MeOH=90:10) yielded 29.7 mg (60%) of the title compound as dark red-violet crystals.

Example 2: Determining Redox Behaviors of the Azo Compounds

The redox behavior of representative azo compounds as described herein was investigated as part of an evaluation on the extent to which azo compounds of the general formula (I) can be used as a mediator in diagnostic methods.

Methods: A solution of 4-[bis-(2-hydroxyethyl)-amino]-benzenediazocarbamide (7) (5 mM in 0.2M potassium phosphate buffer pH 7.0, 0.9% NaCl, 0.5% Triton X-100) was prepared. After adding FAD-dependent glucose dehydrogenase (20 mg/ml), 10 μl of a glucose solution (concentration: 0 mg/dl, 100 mg/dl, 200 mg/dl, 300 mg/dl, 400 mg/dl and 500 mg/dl) was added to 40 μl of this solution and preincubated for 5 min.

Subsequently a cyclovoltagram against Ag/AgCl was recorded. The potential was firstly changed continuously from 0 mV to −800 mV and subsequently back to +800 mV, and finally to −100 mV, and the currents that flowed were measured. The change in potential per unit of time was 100 mV/sec. The results of these measurements are shown in FIG. 1.

Results: As shown in FIG. 1, the cyclovoltagram exhibits a clear graduation of the size of the oxidation peak in the range between 100 mV and 200 mV (reoxidation of the reduced mediator) depending on the respective glucose concentration. These results indicate that azo compounds as described herein can be used as mediators in amperometric or biamperometric glucose determinations.

Example 3: Kinetics of Converting Glucose Using the Azo Compounds

To further evaluate the redox behavior of the azo compounds as described herein, the kinetics of converting glucose solutions of different concentrations was examined in the presence of NAD-dependent glucose dehydrogenase, carbaNAD and 4-[bis-(2-hydroxyethyl)-amino]-benzenediazocarbamide (7).

Methods: A solution of 4-[bis-(2-hydroxyethyl)-amino]-benzenediazocarbamide (7) and carbaNAD (each 25 mM in 0.2M potassium phosphate buffer pH 7.0, 0.9% NaCl, 0.1% Triton X-100) was prepared. After adding NAD-dependent glucose dehydrogenase (20 mg/ml), 10 μl of a glucose solution (concentration: 0 mg/dl, 100 mg/dl, 200 mg/dl, 300 mg/dl, 400 mg/dl and 500 mg/dl) was added in each case to 40 μl of this solution, whereupon carbaNADH was formed by the enzyme/glucose reaction, which in turn resulted in a reduction of the azo-based mediator.

Figure 2:
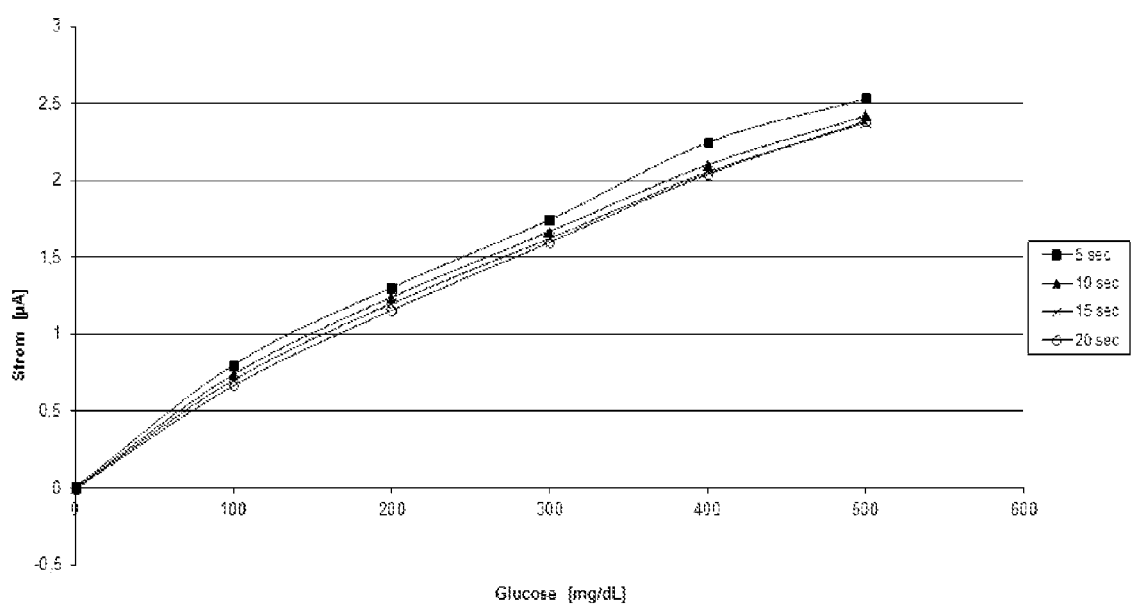
FIG. 2 shows kinetics of converting glucose using the azo-based mediator 4-[bis-(2-hydroxyethyl)-amino]-benzenediazocarbamide (7) in the presence of NAD-dependent glucose dehydrogenase and carbaNAD at glucose concentrations of 0 mg/dl, 100 mg/dl, 200 mg/dl, 300 mg/dl, 400 mg/dl and 500 mg/dl. The current flow after a time period of 5 sec, 10 sec, 15 sec and 20 sec was measured in each case at an applied potential of 200 mV.

The kinetics of the conversion were determined amperometrically immediately after addition of the glucose (i.e., without preincubation). For this purpose, a potential of 200 mV was applied, and the current flowing due to the reoxidation of the azo-based mediator were recorded after a period of 5, 10, 15 and 20 secs. The results of the measurements are shown in FIG. 2.

Results: As shown in FIG. 2, an approximately linear correlation between the glucose concentration and the current measured in each case was seen with short reaction times such as, for example, 5 secs. Hence, the recorded curve can be used as a calibration line for amperometric glucose determinations, which is underlined by the results obtained in Example 2.

Example 4: Kinetics of Reducing the Azo Compounds

To further evaluate the redox behavior of the azo compounds as described herein, the kinetics of the reduction of 4-[bis-(2-hydroxyethyl)-amino]-benzenediazocarbamide (7) was examined using three (3) different reducing agents.

Methods: 1.00 ml of a solution of an acetate salt of 4-[bis-(2-hydroxyethyl)-amino]-benzenediazocarbamide (7) (0.05 M in 0.1 M triethylammonium acetate buffer pH 7) was in each case reacted in a quartz cuvette with 15 equivalents of the reducing agent (e.g., ascorbic acid, carbaNADH (as the disodium salt) or NADH (as the disodium salt); each as a solution in 0.1 M triethylammonium acetate). The individual reaction conditions are summarized in Table 1.

TABLE 1

| # | Azo Mediator | Reducing Agent (RA) | Conc. RA soln. | Vol. RA soln. | Eq. RA |
|---|---|---|---|---|---|
| 1 | 7 | ascorbic acid Na$_2$ | 0.1M | 7.5 μl | 15 |
| 2 | 7 | carbaNADH Na$_2$ | 0.005M | 150 μl | 15 |
| 3 | 7 | NADH Na$_2$ | 0.05M | 15 μl | 15 |

Figure 3A:
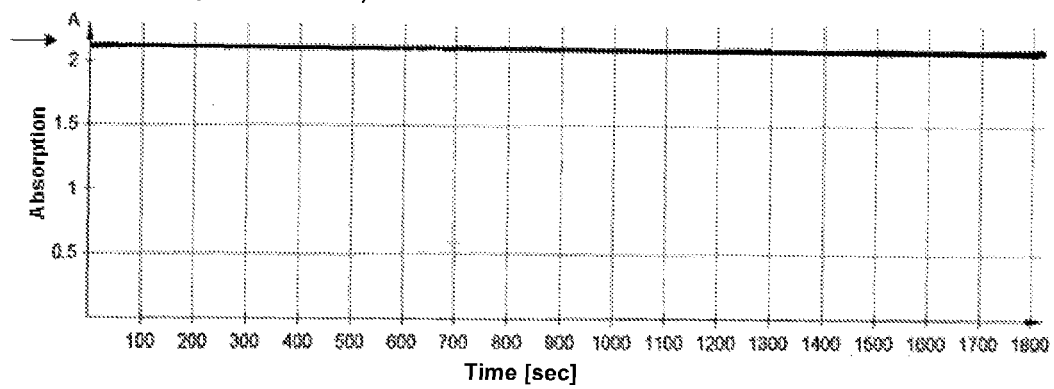
FIG. 3A shows reduction with ascorbic acid (measurement curve is marked with an arrow to make it easier to identify)

The kinetics of the expected reduction of 4-[bis-(2-hydroxyethyl)-amino]-benzenediazocarbamide (7) was recorded immediately after adding the reducing agent by means of UV spectroscopy on the basis of the decrease in the absorption at 500 nm (absorption maximum of the oxidized form of the mediator used) (UV-spectrometer: SPECORD 210, Software: WinASPECT Version 2.2.2.0; Analytik Jena AG). The results of these measurements are shown in FIGS. 3A-3C.

Results: FIG. 3A shows reaction time course in the presence of ascorbic acid and illustrates the insensitivity of 4-[bis-(2-hydroxyethyl)-amino]-benzenediazocarbamide (7) towards this reducing agent. In fact, even after 1800 secs there was no significant decrease in the amount of the oxidized form of the mediator in the time course. The addition of an even larger excess of ascorbic acid after the measuring period led to the same result.

Figure 3B:
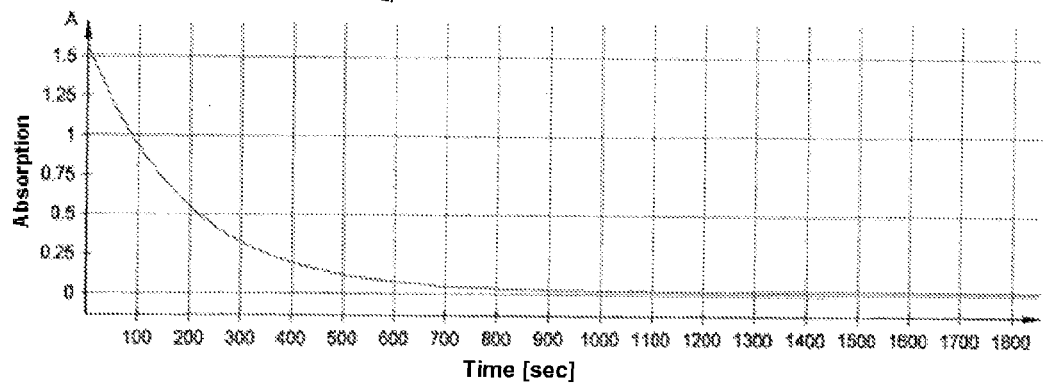
FIG. 3B shows reduction with carbaNADH.
Figure 3C:
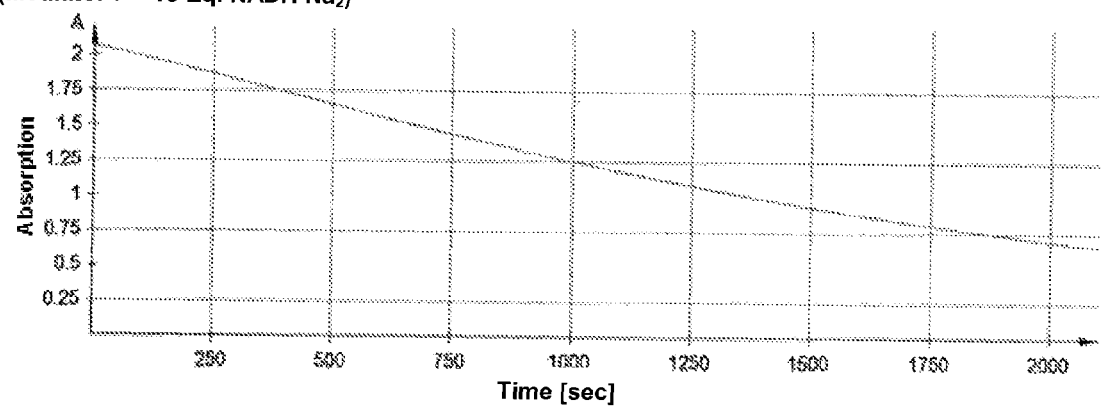
FIG. 3C shows reduction with NADH.

FIGS. 3B and 3C show reaction time courses of reducing 4-[bis-(2-hydroxyethyl)-amino]-benzenediazocarbamide (7) by carbaNADH and NADH, respectively. As shown, carbaNADH, as well as NADH, cause a reduction of the mediator, and a comparison of the two curves allows one to infer a substantially higher reduction rate for the artificial coenzyme carbaNADH.

All of the patents, patent applications, patent application publications and other publications recited herein are hereby incorporated by reference as if set forth in their entirety.

The present inventive concept has been described in connection with what are presently considered to be the most practical and preferred embodiments. However, the inventive concept has been presented by way of illustration and is not intended to be limited to the disclosed embodiments. Accordingly, one of skill in the art will realize that the inventive concept is intended to encompass all modifications and alternative arrangements within the spirit and scope of the inventive concept as set forth in the appended claims.

The invention claimed is:

1. A detection reagent for determining presence or concentration of glucose, the detection reagent comprising:
   (a) a flavine-, nicotinamide- or pyrroloquinoline quinone-dependent oxidoreductase;
   (b) a reducible flavine, nicotinamide or pyrroloquinoline quinone coenzyme;
   (c) an azo compound of the general formula (I):

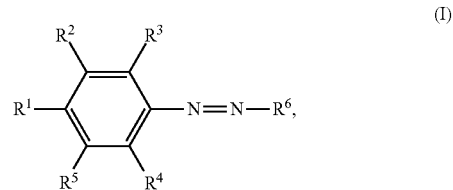

wherein $R^1$ denotes a residue selected from the group consisting of OH, $OR^7$, $SR^7$, $NHR^7$ and $NR^7R^8$;

wherein $R^2$, $R^3$, $R^4$ and $R^5$ independently of one another denote a residue selected from the group consisting of H, alkyl, cycloalkyl, alkenyl, alkynyl, aryl, heterocycloalkyl, heteroaryl, CN, COO$^-$, halogen, O(alkyl), O(aryl), NH(alkyl), N(alkyl)$_2$, N(alkyl)$_3^+$, NH(aryl), N(aryl)$_2$, NO$_2$ and SO$_3^-$, and wherein the alkyl, cycloalkyl, alkenyl, alkynyl, aryl, heterocycloalkyl, heteroaryl, O(alkyl), O(aryl), NH(alkyl), N(alkyl)$_2$, N(alkyl)$_3^+$, NH(aryl) or N(aryl)$_2$ can contain one or more substituents selected from the group consisting of CN, COO$^-$, halogen, NH$_2$, NH(alkyl), N(alkyl)$_2$, N(alkyl)$_3^+$, NH(aryl), N(aryl)$_2$, NH—C(=NH$_2$)—NH$_2^+$, NO$_2$, OH, O—(CH$_2$CH$_2$)$_n$—OH, O—(CH$_2$CH$_2$)$_n$—O(alkyl), O(alkyl), O(aralkyl), O(aryl), OPO$_3^{2-}$, PO$_3^{2-}$ and SO$_3^-$;

wherein $R^6$ denotes a residue selected from the group consisting of CN, C(=X)NH$_2$, C(=X)NHR$^9$, C(=X)NR$^9$R$^{10}$, C(=X)NHOH and C(=X)R$^9$;

wherein $R^7$ and $R^8$ independently of one another denote a residue selected from the group consisting of alkyl, cycloalkyl, alkenyl, alkynyl, aryl, heterocycloalkyl and heteroaryl, and wherein the alkyl, cycloalkyl, alkenyl, alkynyl, aryl, heterocycloalkyl or heteroaryl can contain one or more substituents selected from the group consisting of CN, COO⁻, halogen, $NH_2$, NH(alkyl), $N(alkyl)_2$, $N(alkyl)_3^+$, NH(aryl), $N(aryl)_2$, $NH-C(=NH_2)-NH_2^+$, $NO_2$, OH, $O-(CH_2CH_2)_n-OH$, $O-(CH_2CH_2)_n-O(alkyl)$, O(alkyl), O(aralkyl), O(aryl), $OPO_3^{2-}$, $PO_3^{2-}$ and $SO_3^-$;

alternatively wherein $R^7$ and $R^8$ together with the N atom to which they are bound form a 5-membered to 7-membered heterocycle, and wherein the heterocycle can contain a further heteroatom selected from the group consisting of N, O and S and/or one or more substituents selected from the group consisting of CN, COO⁻, halogen, $NH_2$, NH(alkyl), $N(alkyl)_2$, $N(alkyl)_3^+$, NH(aryl), $N(aryl)_2$, $NH-C(=NH_2)-NH_2^+$, $NO_2$, OH, $O-(CH_2CH_2)_n-OH$, $O-(CH_2CH_2)_n-O(alkyl)$, O(alkyl), O(aralkyl), O(aryl), $OPO_3^{2-}$, $PO_3^{2-}$ and $SO_3^-$;

wherein $R^9$ and $R^{10}$ independently of one another denote a residue selected from the group consisting of alkyl, cycloalkyl, alkenyl, alkynyl, aryl, heterocycloalkyl and heteroaryl, and wherein the alkyl, cycloalkyl, alkenyl, alkynyl, aryl, heterocycloalkyl or heteroaryl can contain one or more substituents selected from the group consisting of CN, COO⁻, halogen, $NH_2$, NH(alkyl), $N(alkyl)_2$, $N(alkyl)_3^+$, NH(aryl), $N(aryl)_2$, $NH-C(=NH_2)-NH_2^+$, $NO_2$, OH, $O-(CH_2CH_2)_n-OH$, $O-(CH_2CH_2)_n-O(alkyl)$, O(alkyl), O(aralkyl), O(aryl), $OPO_3^{2-}$, $PO_3^{2-}$ and $SO_3^-$;

alternatively wherein $R^9$ and $R^{10}$ together with the N atom to which they are bound form a 5-membered to 7-membered heterocycle, and wherein the heterocycle can contain a further heteroatom selected from the group consisting of N, O and S and/or one or more substituents selected from the group consisting of CN, COO⁻, halogen, $NH_2$, NH(alkyl), $N(alkyl)_2$, $N(alkyl)_3^+$, NH(aryl), $N(aryl)_2$, $NH-C(=NH_2)-NH_2^+$, $NO_2$, OH, $O-(CH_2CH_2)_n-OH$, $O-(CH_2CH_2)_n-O(alkyl)$, O(alkyl), O(aralkyl), O(aryl), $OPO_3^{2-}$, $PO_3^{2-}$ and $SO_3^-$;

wherein X denotes a heteroatom selected from the group consisting of O and S, and wherein n denotes an integer from 1 to 6; and (d) optionally a reducible optical indicator.

2. The detection reagent of claim 1, wherein the flavine-, nicotinamide- or pyrroloquinoline quinone-dependent oxidoreductase is a flavine-, nicotinamide- or pyrroloquinoline quinone-dependent dehydrogenase.

3. The detection reagent of claim 2, wherein the flavine-, nicotinamide- or pyrroloquinoline quinone-dependent glucose dehydrogenase is a glucose-6-phosphate dehydrogenase.

4. The detection reagent of claim 1, wherein the reducible flavine, nicotinamide or pyrroloquinoline quinone coenzyme is selected from the group consisting of carbaNAD⁺, carbaNADP⁺, FAD, FMN, NAD⁺, NADP⁺, PQQ and derivatives thereof.

5. The detection reagent of claim 1, wherein the azo compound is 4-[bis-(2-hydroxyethyl)-amino]-benzenediazocarbamide.

6. A kit for determining presence or concentration of glucose, the kit comprising:
   (a) the detection reagent of claim 1; and
   (b) an optical test element or an electrochemical test element.

7. A test element for determining presence or concentration of glucose, the test element comprising the detection reagent of claim 1.

8. The test element of claim 6, wherein the test element is an optical sensor or an electrochemical sensor.

9. A method of determining presence or concentration of glucose, the method comprising the steps of:
   (a) contacting a sample comprising glucose with the test element of claim 7; and
   (b) determining a presence and/or a concentration of glucose in the sample.

* * * * *